United States Patent [19]

Chiknas

[11] Patent Number: 5,490,981
[45] Date of Patent: Feb. 13, 1996

[54] DIAGNOSTIC AND THERAPEUTIC COMPOSITIONS AND METHODS FOR LIPOPROTEIN(A)

[75] Inventor: Steven G. Chiknas, Vienna, Va.

[73] Assignee: John E. Carbaugh, Jr., Rosslyn, Va.

[21] Appl. No.: 234,602

[22] Filed: Apr. 28, 1994

Related U.S. Application Data

[63] Continuation of Ser. No. 86,358, Jul. 6, 1993, abandoned, which is a continuation of Ser. No. 832,994, Feb. 10, 1992, abandoned, which is a division of Ser. No. 619,525, Nov. 29, 1990, abandoned.

[51] Int. Cl.$^6$ .................. A61K 39/385; A61K 38/10; C07K 17/02; C07K 14/775
[52] U.S. Cl. .................. 424/194.1; 424/193.1; 530/323; 530/326; 530/359; 435/961
[58] Field of Search .................. 424/193.1, 194.1; 530/323, 326, 359; 435/961

[56] References Cited

U.S. PATENT DOCUMENTS

| | | | |
|---|---|---|---|
| 4,677,057 | 6/1987 | Curtiss et al. | 435/7 |
| 4,828,986 | 5/1989 | Smith et al. | 435/7 |
| 4,945,040 | 7/1990 | Fless et al. | 435/7 |
| 4,970,144 | 11/1990 | Fareed et al. | 435/5 |
| 5,126,240 | 6/1992 | Curtiss | 435/7.94 |

OTHER PUBLICATIONS

Taimn (1989), Methods Enzymol 168: 7–15.
Posnett et al (1989) Methods Enzymol 178: 739–746.
McLean et al (1987) Nature 330: 132–137.
Tomlinson et al (1989) J. Biol. Chem. 264(10): 5957–5965.
Salonen et al (1989) The EMBO J. 8(13): 4035–4040.

*Primary Examiner*—Kay K. A. Kim
*Attorney, Agent, or Firm*—Wenderoth, Lind & Ponack

[57] ABSTRACT

Peptides which present an epitope substantially similar to the activation site region epitope of apolipoprotein(a) are provided. Antibodies raised against such peptides bind to apolipoprotein(a). Such antibodies and peptides, as well as peptide constructs for immunization are provided. Also provided are monoclonal antibodies and hybridomas, polyclonal serum, assays, diagnostic systems in kit form, chromatographic methods and materials, and synthetic secondary standards. Therapeutic compositions and methods are also provided.

1 Claim, 1 Drawing Sheet

DIAGNOSTIC AND THERAPEUTIC COMPOSITIONS AND METHODS FOR LIPOPROTEIN(A)

This application is a continuation of now abandoned application, Ser. No. 08/086,358, filed Jul. 6, 1993, which is a continuation of now abandoned application Ser. No. 07/832,994, filed Feb. 10, 1992, which is a divisional application of now abandoned Ser. No. 07/619,525, filed Nov. 29, 1990.

FIELD OF THE INVENTION

This invention relates to diagnostic products and methods for determining the presence of lipoprotein(a) or apolipoprotein(a) in a fluid sample such as a blood sample. This invention also relates to therapeutic compositions and methods for decreasing the presence of lipoprotein(a) in a mammal or generating an immune response to lipoprotein(a).

BACKGROUND OF THE INVENTION

Lipoproteins are the primary carriers of plasma cholesterol. They are micellar lipid-protein complexes (particles) having a surface film, comprised of one or more proteins associated with polar lipids, that surround a cholesterol-containing core. Lipoproteins were originally classified based on their buoyant densities as measured by ultracentrifugation. Accordingly, four major density classes have been recognized: chylomicrons, very low-density lipoproteins (VLDL), low-density lipoproteins (LDL) and high-density lipoproteins (HDL).

Studies have established a direct correlation between plasma LDL cholesterol levels and the risk of coronary artery disease (CAD). That is, elevated levels of plasma cholesterol found in LDL particles correlate with an increased risk of CAD. Similarly, many studies have now shown that elevated plasma levels of lipoprotein(a), a component of LDL, evidence a high risk factor for heart disease and atherosclerosis.

The structure of the lipoprotein(a) molecule has been determined to comprise a protein portion identified as apolipoprotein B-100 linked through disulfide bonds to two apolipoprotein(a) molecules. The structure of lipoprotein(a) is similar to that of plasminogen, a blood component involved in vessel wound repair which is activated by proteolytic cleavage at a specific activation site by tissue-type plasminogen activator (t-PA) or urokinase. The region encompassing the plasminogen activation site ("activation site region") differs in amino acid sequence the analogous apolipoprotein(a) region. The sequence around the plasminogen activation site (arginine-valine) is (SEQ ID NO:5) LYS-CYS-PRO-GLY-ARG-VAL-VAL-GLY-GLY, whereas the analogous apolipoprotein(a) sequence is (SEQ ID NO:6) LYS-CYS-PRO-GLY-SER-ILE-VAL-GLY-GLY. See Eaton et al., *Proc. Natl. Acad. Sci. USA*, 84: 3224–3228, 3227 (1987), the disclosure of which is incorporated herein. Moreover, while plasminogen is activated by cleavage by urokinase or t-PA at arginine 560, apolipoprotein(a) may be inactive or not activatable by streptokinase, urokinase or t-PA. Id. For purposes of this disclosure, the above-described region of apolipoprotein(a) that is analogous to the activation site region of plasminogen will be hereinafter referred to as "the activation site region of apolipoprotein(a)."

Despite these differences in the plasminogen and analogous apolipoprotein(a) activation site regions, the amino acid sequence of lipoprotein(a) and plasminogen are considerably homologous, each having long, recurring sequences of amino acids called "kringles." Previous attempts to prepare lipoprotein(a) assays have utilized antibodies raised against the entire lipoprotein(a) molecule. The apolipoprotein(a) can be purified by known centrifugation methods, and the purified protein is then injected into animals to raise antibodies. Because of the considerable structural homology between lipoprotein(a) and plasminogen, most of the antibodies raised against the entire lipoprotein(a) molecule have recognized epitopes common to both lipoprotein(a) and plasminogen, i.e., the antibodies cross react with plasminogen. Consequently, such assays have met with limited success because of the low number of antibodies which do not cross react with plasminogen, and because of the uncertainty regarding what those few antibodies which do not cross react are binding to. Further, the ability to perform assays for apolipoprotein(a) have been hampered by the lack of standards against which assay results can be accurately compared.

Thus, it has not been easy to directly assay a serum sample for lipoprotein(a) because the plasminogen present in the serum yields a false positive result. For this reason, there is a continuing need for means to determine the presence or absence of lipoprotein(a) in a serum sample without the problem of false positive results due to plasminogen, and a continuing need for a standard against which assay results can be accurately measured.

SUMMARY OF THE INVENTION

Accordingly, it is an object of this invention to provide an assay for detecting and/or quantifying the presence of lipoprotein(a) or apolipoprotein(a) in a serum sample, which assay minimizes the inteference caused by the presence of plasminogen in the sample.

It is also an object to provide peptides that are useful in such assays and for preparing antibodies for carrying out such assays. It is also an object to provide standards against which assay results can be accurately compared.

It is a further object to provide compositions and methods for chromatographically separating lipoprotein(a) or apolipoprotein(a) from a sample.

It is also a further object to provide therapeutic compositions and methods for treating mammals in which lipoprotein(a) is present.

In achieving these objects, there has been provided, in accordance with one aspect of this invention, a peptide which presents an epitope substantially similar to an epitope presented by the activation site region of apolipoprotein(a), wherein antibodies which bind to said peptide also bind to said epitope of said activation site region. In a preferred embodiment, the peptide comprises amino acid residues of the sequence SER-ILE, or its immunological equivalent.

In accordance with another aspect of this invention, a peptide is provided that comprises amino acid residues of the following sequence: (SEQ ID NO:1)

GLU-PRO-LYS-LYS-CYS-PRO-GLY-SER-ILE-VAL-GLY-GLY-CYS-VAL-ALA or its immunological equivalent.

Other aspects of this invention provide peptide constructs comprising a carrier onto which is bound a peptide as described above.

Another embodiment of this invention provides a process for preparing an antibody which binds to an epitope presented by the activation site region of apolipoprotein(a). The process comprises immunizing an animal or mammal with a peptide construct as described above, and harvesting the antibodies produced. An antibody so produced by this process is also contemplated.

In this regard, antibodies which recognize the above-described peptides, including monoclonal antibodies, are also contemplated. Hybridomas that produce such monoclonal antibodies are also contemplated. Preferred embodiments include antibodies which exhibit substantially no cross reactivity with plasminogen.

Other embodiments of this invention include assays for determining the presence of lipoprotein(a) or apolipoprotein(a) in a sample. The assays comprise the steps of: contacting the sample with a first antibody which binds to an epitope of the activation site region of apolipoprotein(a); maintaining the first antibody in contact with the sample for a time sufficient to form an apolipoprotein(a)-first antibody reaction product; and then determining whether any apolipoprotein(a)-first antibody reaction product is present.

Other contemplated embodiments of this invention comprise assays for lipoprotein in a sample, wherein the improvement comprises the use of an antibody which binds to an epitope of the activation site region of apolipoprotein(a).

Other contemplated embodiments of this invention comprise diagnostic systems, in kit form, including reagents capable of performing the aforementioned assays.

Other contemplated embodiments comprise synthetic secondary standard peptides against which assay results can be accurately measured. The standards comprise first and second regions separated by a linkage region. The first region comprises amino acid residues in a sequence which will bind a first antibody, and the second region comprises amino acid residues which will bind a second antibody. The linkage region is comprised of a material (e.g., amino acid residues) to which the first and second antibodies will not bind, and is of sufficient length to minimize steric hindrance in the binding of the first and second antibodies to the first and second regions.

Yet other embodiments of this invention comprise a method of chromatographically separating lipoprotein(a) or apolipoprotein(a) from a sample utilizing the above-described antibodies, and chromatographic material comprising such antibodies.

Still other embodiments contemplated by this invention include therapeutic compositions comprising antibodies of this invention, and antibody conjugates comprising the antibodies of this invention. Such conjugates can comprise, for example, an agent which cleaves or otherwise alters lipoprotein(a), or which provokes an immune response to the lipoprotein(a)-conjugate complex per se. The peptides of this invention can be used to provoke an immune response to lipoprotein(a). Methods of reducing the presence of lipoprotein(a) in a mammal using such therapeutic compositions are also provided.

Additional objects and advantages of the invention will be set forth in part in the description that follows, and in part will be obvious from the description, or may be learned by practice of the invention. The objects and the advantages of this invention may be realized and obtained by means of the compositions of matter and processes particularly pointed out in the appended claims.

DESCRIPTION OF THE PREFERRED EMBODIMENTS

Figure 1:
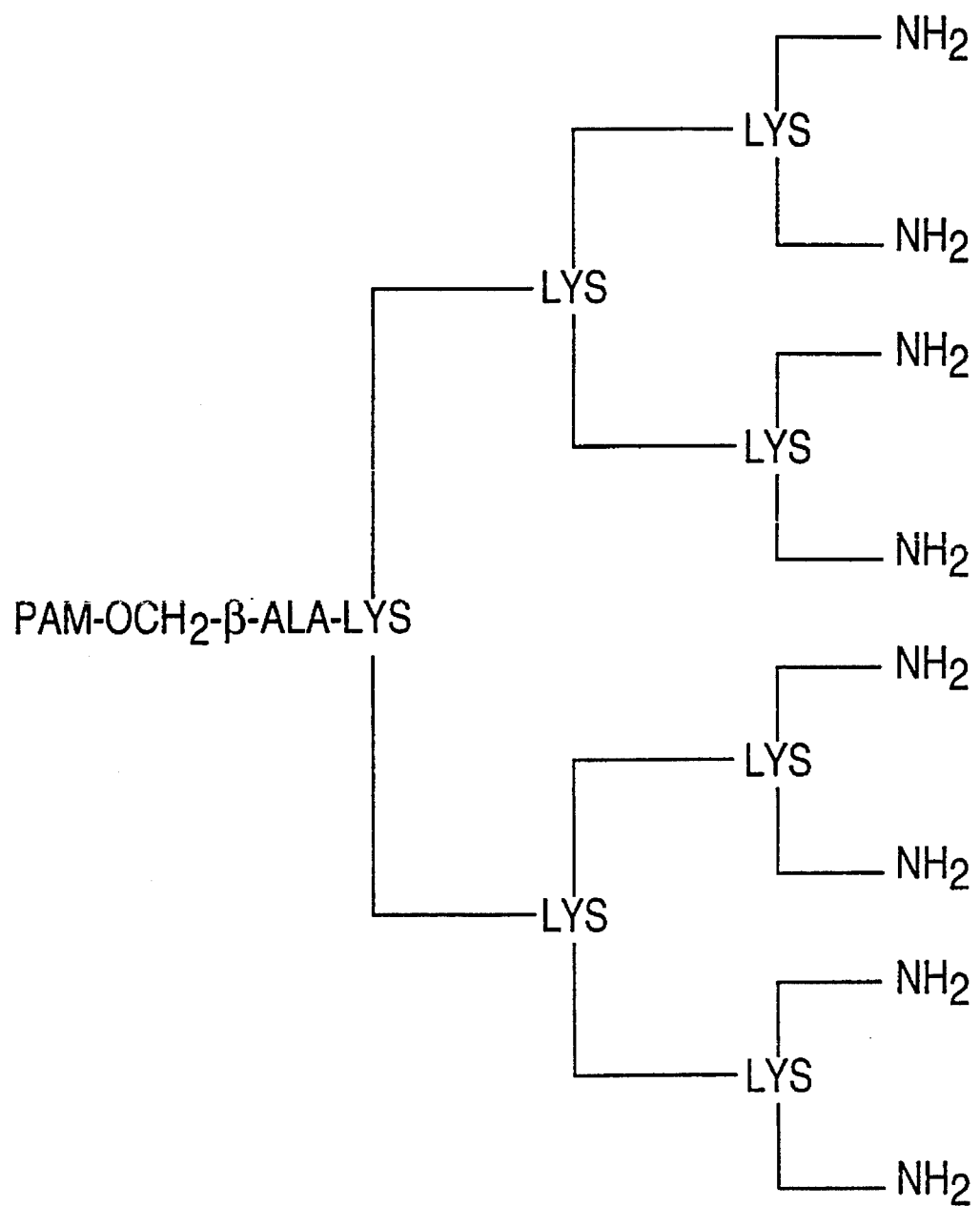
FIGURE 1 illustrates the proposed structure of a lysine backbone of a peptide construct core in accordance with this invention.

Surprisingly, it has been discovered that the activation site region of apolipoprotein(a) presents an epitope such that antibodies raised against a peptide that is substantially similar to this epitope will recognize and bind native apolipoprotein(a). In particular, a peptide that comprises a serine-isoleucine (SER-ILE) sequence or its immunological equivalent, together with sufficient adjacent amino acid residues from the apolipoprotein(a) activation site region or their immunological equivalents to form an epitope substantially similar to that presented by the activation site region of apolipoprotein(a), can be used to raise antibodies which will recognize and bind apolipoprotein(a). Further, it has been discovered that antibodies raised against a peptide within this invention may exhibit little or no cross reactivity with plasminogen and, hence, are useful in assaying for or separating lipoprotein(a) in or from serum.

Based on this discovery, assays for lipoprotein(a) can now be performed without the problem of plasminogen interference. At least two basic types of assays can thus be performed in accordance with this invention. In the first, a protease (e.g., urokinase, streptokinase or tPA), which recognizes the activation site of plasminogen but not that of apolipoprotein(a), can be added to the serum sample to be assayed. The plasminogen is cleaved and thus presents no epitope similar to that of the activation site region of apolipoprotein(a). Therefore, even if the antibodies which have been raised against the peptides of this invention do exhibit cross reactivity with plasminogen, the only intact activation site region present in the sample after addition of enzyme will be that of apolipoprotein(a). Thus, the antibodies substantially will bind only to apolipoprotein(a).

In the other basic type of assay, antibodies which substantially do not cross react with plasminogen are used. In such assays, there is no need first to treat the sample with a protease to cleave the plasminogen. Instead, using conventional assay formats, the sample can be immediately assayed for apolipoprotein(a) without the problem of plasminogen interference. The selection of such antibodies is discussed below.

Both of the foregoing types of assays are contemplated and within the scope of this invention. Those of ordinary skill may readily appreciate other types of assays which can also be carried out using the biological products taught herein. Many different types of assay formats—sandwich, competitive, precipitation, homogeneous, heterogenous, etc.—can be used for the foregoing types of assays.

A. Definitions

The following definitions are provided for some of the terms used throughout this specification.

Amine Acid Residues—identified herein are in the natural L-configuration. The following abbreviations for amino acid residues are used:

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |

-continued

| SYMBOL | | |
|---|---|---|
| 1-Letter | 3-Letter | AMINO ACID |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine, |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid residue sequences are represented herein by formulae whose left to right orientation is in the conventional direction of amino-terminus to carboxyterminus.

Peptide—is used herein to designate a linear series of amino acid residues connected one to the other by peptide bonds between the alpha-amino and carboxy groups of adjacent residues. Peptide, as used herein, does not refer to a naturally occurring protein such as lipoprotein(a) or apolipoprotein(a).

Protein—refers to any naturally occurring combination of amino acid residues.

Antibody—in its various grammatical forms is used herein as a collective noun that refers to a population of immunoglobulin molecules and/or immunologically active portions of immunoglobulin molecules, i.e., molecules that contain an "antigen binding site" or paratope. An antigen binding site is that structural portion of an antibody molecule that specifically binds an antigen.

Exemplary antibodies are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies can be prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. Antibodies and binding fragments can also be produced by recombinant methods, which are well known to those skilled in the art. See, for example, U.S. Pat. No. 4,946,778 to Ladner et al.

The antibodies may also be catalytic antibodies, which are capable of binding to the protease site of apolipoprotein(a) and catalyzing a reaction. Catalytic antibodies are well known to those skilled in that art; see, for example, "Catalytic Antibodies," C&EN, pp 26–40 (May 28, 1990), the disclosure of which is incorporated herein.

Polyclonal serum—refers to serum comprising antibodies generated by one or more animals in response to being injected with the peptide constructs of this invention.

Monoclonal antibody—in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore comprise an antibody molecule having a plurality of antibody combining sites, each immunospecific for a different antigen, e.g., a bispecific or "bifunctional" monoclonal antibody.

Methods for determining the affinity of a monoclonal antibody for an antigen and comparing those affinities for equivalence are well known in the art. See, for example, Muller, *J. Immunol. Meth.*, 34:345352 (1980) and Sokal et al., *Biometry.*, W. H. Freeman & Co., (1981).

B. The Peptides

In order to construct a diagnostic immunoassay capable of identifying the presence and, optionally, the quantity of lipoprotein(a) in blood plasma, an immunological means such as an antibody is required for separating the lipoprotein(a) from other blood components. For the antibody to be effective in binding lipoprotein(a), it must be directed to an epitope appearing on the surface of the molecule. With lipoproteins, where the surface proteins surround and are imbedded in globules of lipid in a dynamic state, it is desirable to select antibodies against epitopes which are on the surface of the lipids substantially at all times.

Further, in a molecule such as lipoprotein(a) where the primary structure is associated in a variable number of repetitious segments called "kringles" which vary in number and surface availability, the selection of an epitope which appears only once in each molecule acquires added importance. Further still, in a serum assay for lipoprotein(a) or apolipoprotein(a), it may be desirable that the antibodies used substantially will not cross react with plasminogen present in the serum sample.

It has been discovered that antibodies raised against a peptide which presents an epitope substantially similar to the epitope presented by the activation site region of apolipoprotein(a) can apparently satisfy all of the foregoing criteria.

In accordance with the foregoing, a peptide which presents an epitope substantially similar to an epitope of the activation site region in apolipoprotein(a) can be synthesized. A peptide in accordance with this invention can first comprise a serine-isoleucine (SER-ILE) sequence or its immunological equivalent. The peptide can also comprise one or several amino acid residues adjacent to either or both the serine and isoleucine. The adjacent residues should comprise amino acid residues from the activation site region of apolipoprotein(a) or their immunological equivalents. By immunological equivalent, it is meant that certain amino acid residue substitutions and/or deletions can possibly be made in peptides which repeat part or all of the activation site region sequence of apolipoprotein(a), and yet the new peptide will provoke a substantially similar immune response. Such substitutions and/or deletions can be made in accordance with established principles, some of which are briefly discussed below, to yield a peptide which can be used to raise antibodies which behave substantially the same as antibodies raised against a peptide having the natural sequence. In this regard, antibodies which bind to an epitope of the activation site region of apolipoprotein(a) are considered to be equivalents. Thus, to be a immunological equivalent, it is not necessary that each residue of the natural apolipoprotein(a) activation site region sequence or fragment thereof be replaced with an immunologically equivalent residue, but rather that the peptide as a whole evokes a substantially similar immune response.

Thus, in a peptide in accordance with this invention, the serine (of the serine-isoleucine dimer) or an immunological equivalent of the serine can, for example, have attached to it the following residues or their immunological equivalents:

|                                                      |
| ---------------------------------------------------- |
| GLY- |
| PRO-GLY- |
| CYS-PRO-GLY- |
| (SEQ ID NO:7) |
| LYS-CYS-PRO-GLY- |
| (SEQ ID NO:8) |
| LYS-LYS-CYS-PRO-GLY- |
| (SEQ ID NO:9) |
| PRO-LYS-LYS-CYS-PRO-GLY- |
| (SEQ ID NO:10) |
| GLU-PRO-LYS-LYS-CYS-PRO-GLY- | and so forth. Similarly, the isoleucine of the serine-isoleucine dimer, or the immunological equivalent of isoleucine can, for example, have attached to it the following residues or their immunological equivalents:

|                                                      |
| ---------------------------------------------------- |
| -VAL |
| -VAL-GLY |
| -VAL-GLY-GLY |
| (SEQ ID NO:11) |
| -VAL-GLY-GLY-CYS |
| (SEQ ID NO:12) |
| -VAL-GLY-GLY-CYS-VAL |
| (SEQ ID NO:13) |
| -VAL-GLY-GLY-CYS-VAL-ALA | and so forth. Alternatively, the above residues can be attached onto one or more amino acid residues which present an immunological equivalent to the SER-ILE dimer itself, or the corresponding residues can be attached onto one or more amino acid residues which present an immunological equivalent to the GLY-SER-ILE or SER-ILE-VAL trimers, and so forth (e.g., tetramers, pentamers, etc.). Likewise, preparation of many other permutations and combinations within the scope of this invention is well within the ordinary skill in this art, and determining which peptides evoke the desired immune response will involve only routine experimentation.

Thus, substitutions of one amino acid for another, either conservative or non-conservative, where such changes provide for certain advantages in their use are contemplated. Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. Conservative substitutions also include the use of a substituted amino acid in place of an unsubstituted parent amino acid provided that such a peptide also displays the requisite binding activity.

A peptide in accordance with this invention which has a sequence that is not identical to the sequence of the activation site region of apolipoprotein(a) (because one or more conservative or nonconservative substitutions and/or deletions have been made) will usually have no more than about 30 number percent, advantageously no more than about 20 number percent, and preferably no more than about 10 number percent of the amino acid residues which comprise all or part of the activation site region of apolipoprotein(a) substituted or deleted, except where additional residues have been added at either terminus for the purpose of providing a "linker" by which the peptides of this invention can be conveniently affixed to a label, a solid matrix, or a carrier. Labels, solid matrices and carriers that can be used with the peptides of this invention are described below.

Amino acid residue linkers usually comprise at least one amino acid residue and can comprise 40 or more residues, more often 1 to 10 residues. The linker residues do not form lipoprotein(a) epitopes, i.e., they are not similar is structure to the lipoprotein(a). Typical amino acid residues used for linking are glycine, alanine, serine, threonine, or the like. In addition, the amino acid residue sequence of a peptide in accordance with this invention can differ, unless otherwise specified, from the natural sequence of the activation site region of apolipoprotein(a) by the sequence being modified by terminal-NH$_2$ acylation, e.g., acetylation.

The length of the peptides of this invention can vary, for example, depending on the type of carrier used for immunization. It is generally preferred that the peptide be of a length which minimizes the number of epitopes other than the desired epitope so that the population of antibodies raised against the peptide will contain a greater concentration of the desired antibodies. Moreover, when preparing the peptides by chemical synthesis, additional residues will generally lengthen the time required for their preparation. Peptides which also present epitopes in addition to that of the apolipoprotein(a) activation site region are, however, certainly also within the scope of this invention. Routine experimentation will yield the optimum length(s).

As but one example, it has been found that a peptide having the following sequence of amino acid residues: (SEQ ID NO:1) GLU-PRO-LYS-LYS-CYS-PRO-GLY-SER-ILE-VAL-GLY-GLY-CYS-VAL-ALA is very useful in preparing antibodies which bind to the activation site region of apolipoprotein(a). The length was chosen because of the type of peptide construct which was to be used.

A peptide in accordance with this invention can be synthesized by any of the techniques that are known to those skilled in the peptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis," W. H. Freeman Co., San Francisco, (1969); M. Bodanszky et al., "Peptide Synthesis," John Wiley & Sons, Second Edition, (1976); and J. Meienhofer, "Hormonal Proteins and Peptides," Vol 2, p. 46, Academic Press, New York ., , , (1983) for solid phase peptide synthesis, and E. Schroder and K. Kubke, 1 THE PEPTIDES, Academic Press, New York (1965) for classical solution synthesis, each of which is incorporated herein by reference. Appropriate protective groups usable in such synthesis are described in the above texts and in J. F. W. McOmie, PROTECTIVE GROUPS IN ORGANIC CHEMISTRY, Plenum Press, New York (1973), which is also incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final peptide.

C. The Peptide Constructs

When coupled to a carrier to form a peptide construct, the peptides of this invention are capable of inducing antibodies that bind to the activation site region of apolipoprotein(a). The preparation of peptide constructs is well known to those skilled in that art. While many different types of constructs are contemplated, preferred constructs have been assembled according to the Multiple Antigen Peptide System of Tam et al, "Synthetic Peptide Vaccine Design," *Proc. Natl. Acad. Sci. USA*, 85: 5409–5413 (August 1988). It has been found that constructs prepared in accordance with the procedure of Tam et al. yield sera comprising antibodies which are highly specific for lipoprotein(a).

Following the procedure of Tam et al. a construct in accordance with this invention having a molecular weight of about 12,000 daltons was prepared. (See Examples 1–3.) The construct comprised a core of 7 lysine residues containing 8 copies of the peptide each separated from the core by a tri-glycine extender and has the following structure:

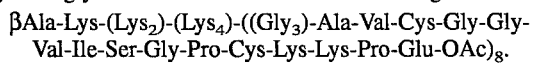

The construct was generally prepared as follows. First, a core consisting of 7 lysine residues was constructed on a base of βAla-OCH$_2$-Pam resin according to the manual synthesis method of Merrifield (*J. Amer. Chem. Soc.* 85, 2149–2154 (1963)). A triglycyl linker was then added followed by the sequential addition of the amino acids in the peptide chain. The chains were acetylated on their —NH$_2$ terminal ends prior to removal from the Pam resin to decrease the total charge present on the construct. The constructs were monitored closely during the sequential addition of amino acids to assure better than 99% coverage of free amino groups to minimize deletion peptides, which are difficult or impossible to detect in the finished construct. The constructs were then dialyzed extensively following removal from the resin in denaturing and reducing conditions to remove any byproducts of the cleavage reaction. The constructs were then lyophilized and utilized for inoculations in complete Freund's adjuvant without further purification.

An amino acid analysis of the peptide construct was performed. The presence of free sulfhydryl groups was demonstrated by dinitrobenzene analysis (*J. Biochem.*, 89:296 (1963)). An agarose electrophoresis was performed, which, upon staining for protein utilizing Sudan black, demonstrated a single diffuse band.

In addition to being useful for raising antibodies, the peptide constructs of this invention are useful for assays such as ELISA testing for lipoprotein(a) and apolipoprotein(a) antibodies and for affinity purification of lipoprotein(a) and apolipoprotein(a) antibodies, and for use in provoking immune responses against lipoprotein(a) in mammals. Other uses will be readily apparent to those skilled in the art.

D. The AntiBodies

As stated above, antibodies in accordance with this invention are those which bind to an epitope on the activation site region of apolipoprotein(a). Substantially purified quantities of monoclonal or polyclonal antibodies can thus be prepared. Such antibodies may exhibit some affinity toward plasminogen. Their affinity to plasminogen, however, preferably will be small in comparison to their affinity to lipoprotein(a) and apolipoprotein(a). For example, preferred antibodies in accordance with this invention are those which exhibit an affinity to apolipoprotein(a) that is greater than their affinity to plasminogen by a factor of 2, 5, 10, 100, 1000, 10000 or more.

Methods for preparing antibodies from constructs such as those described above are well known and are not repeated in detail here. Polyclonal sera can be obtained, for example, from mice that have been immunized with such constructs. (See Example 4.) Monoclonal antibodies can then be prepared using routine methods, for example, from cells obtained from the immunized mice. (See Example 5.) Exemplary procedures for obtaining monoclonal antibodies and hybridomas in accordance with this invention are as follows. Other procedures may be known to those skilled in that art.

A monoclonal antibody in accordance with this invention, typically containing whole antibody molecules, can be prepared using the peptide-induced hybridoma technology described by Niman et al., *Proc. Natl. Sci., USA*, 80:4949–4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a peptide of this invention.

It is preferred that the myeloma cell line be from the same species as the lymphocytes. Typically, a mouse, for example of the strain 129 GlX+, is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention can be identified by an assay such as a radioimmunoassay (RIA) or a sandwich assay.

A monoclonal antibody of the present invention can be produced by initiating a monoclonal hybridoma culture comprising a nutrient medium containing a hybridoma that secretes antibody molecules of the appropriate peptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

The monoclonal antibody produced by the above method can be used, for example, in diagnostic and therapeutic modalities wherein formation of an lipoprotein(a)- or apolipoprotein(a)-containing immunoreaction product is desired.

Antibodies in accordance with this invention can be screened according to their affinities to (1) the peptides against which they were raised, (2) lipoprotein(a) or apolipoprotein(a), and/or (3) plasminogen. Preferred antibodies will exhibit high affinities for lipoprotein(a) or apolipoprotein(a), low affinities for plasminogen, and at least some affinity for the peptide against which they were raised.

E. Assays and Diagnostic Systems

The present invention contemplates various immunoassay methods for determining the amount of lipoprotein(a) or apolipoprotein(a) in a biological fluid sample using a peptide and/or antibodies of this invention. The peptide or antibody comprises immunochemical reagents for forming an immunoreaction product whose presence or amount relates, either directly or indirectly, to the presence or amount of lipoprotein(a) or apolipoprotein(a) in the sample. Those skilled in the art will appreciate that there are numerous well known clinical diagnostic chemistry procedures in which the immunochemical reagents of this invention can be used to form an immunoreaction product whose presence and/or amount relates to the presence and/or amount of lipoprotein(a) or apolipoprotein(a) present in a body sample.

Thus, while exemplary assay methods are described herein, the invention is not so limited. Various heterogenous and homogeneous protocols, either competitive or noncompetitive, can be employed in performing an assay method of this invention. As stated above, the assays of this invention can also utilize a protease such as urokinase, streptokinase or t-PA for treating the sample to cleave any plasminogen present. Such a step may always be used and those of ordinary skill will readily appreciate the manner in which such proteases may be employed. It may, however, be preferable in terms of time, simplicity and expense to use such proteases only when the antibodies used exhibit more than minimal affinity toward plasminogen.

For example, the present invention contemplates a double antibody or "sandwich" immunoassay comprising the steps of: (a) forming a first immunoreaction admixture by admixing a vascular fluid sample with a first antibody, e.g., a monoclonal antibody, wherein the antibody and apolipoprotein(a) present in the sample are capable of forming a first immunoreaction product (the first antibody can be operatively linked to a solid matrix); (b) maintaining the first immunoreaction admixture so formed under biological assay conditions for a time period sufficient to form the first immunoreaction product (the first immunoreaction product can then been separated from the sample); (c) forming a second immunoreaction admixture by admixing the first immunoreaction product with a second antibody, monoclonal or polyclonal, which recognizes lipoprotein(a) or apolipoprotein(a); (d) maintaining the second immunoreaction admixture so formed under biological assay conditions for a period sufficient to form the second or "sandwich" immunoreaction product; and (e) determining the presence and, optionally, the amount of second immunoreaction product formed, and thereby the presence and, optionally, the amount of lipoprotein(a) or apolipoprotein(a) in the sample.

Preferably, the second antibody is labeled, preferably with an enzyme, and thus the second immunoreaction product formed will be a labeled product.

In preferred double antibody assay methods, the amount of immunoreaction product determined is related to the amount of immunoreaction product similarly formed and determined using a standard sample in place of the vascular fluid sample, wherein the standard sample contains a known amount of lipoprotein(a) or apolipoprotein(a) in accordance with this invention. Alternatively, a synthetic secondary standard (see, e.g., Example 11) can be used.

It is also preferred that the second antibody be directed to a site on the lipoprotein(a) or apolipoprotein(a) which is not the same as the site to which the first antibody is directed, i.e., not the activation site region of apolipoprotein(a). For example, the second antibody can be an anti-B-100 antibody, an anti-plasminogen antibody, or another anti-apolipoprotein(a) antibody directed to a site other than the activation site region of apolipoprotein(a), e.g., the N-terminal or C-terminal.

The vascular fluid sample can be provided as a known or unknown quantity of blood, or a blood derived product such as serum or plasma. The amount of antibody used can be known or unknown. The admixture is maintained under biological assay conditions for a predetermined period of from about a few seconds to about 20 hours at a temperature of from about 4 degrees C. to about 45 degrees C., advantageously room temperature, i.e., about 25 degrees C.

Biological assay conditions are those that maintain the biological activity of the immunochemical reagents of this invention and the lipoprotein(a) and apolipoprotein(a). Those conditions can generally include a temperature range of from about 4 to about 45° C., a pH value range of from about 5 to about 9, and an ionic strength varying from about that of distilled water to about one molar sodium chloride. Upon routine experimentation, other biological assay conditions may be learned. Methods for optimizing such conditions are well known to those skilled in the art.

Another assay format that is preferred is the precipitation assay. In this embodiment, the process comprises formation of an immunoreaction admixture by admixing a vascular fluid sample with a first antibody (which can be from polyclonal sera) to yield an precipitous immunoreaction product. The antibody can be operatively linked to a solid particulate such as a microparticle or bead, such that when antibody-antigen crosslinking occurs, the particulate matter aggregates, indicating the presence of the target material.

Many other types of assays within the scope of this invention will be readily apparent to those skilled in the art.

A diagnostic system, in kit form, of the present invention generally comprises, in an amount sufficient for at least one assay, an antibody within the scope of this invention and a means for detecting an immunoreaction product comprising the antibody and apolipoprotein(a) as packaged immunochemical reagents. Instructions for use of a packaged immunochemical reagent are also typically included.

As used herein, the term "packaged" can refer to the use of a solid matrix or material such as glass, plastic, paper, fiber, foil and the like capable of holding within fixed limits an antibody of this invention. Thus, for example, a package can be a glass vial used to contain milligram quantities of a contemplated antibody or it can be a microtiter plate well to which microgram quantities of a contemplated antibody has been operatively affixed. Alternatively, a package could include antibody-coated microparticles entrapped within a porous membrane or imbedded in a test strip or dipstick, etc. Alternatively, the antibody can be directly coated onto a membrane, test strip or dipstick, etc. which contacts the sample fluid. Many other possibilities exist and will be readily recognized by those skilled in this art.

Instructions for use typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing an antibody of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, peptide, or antibody molecule that is part of the present invention, or used separately, and those atoms or molecules can be used alone or in conjunction with additional reagents. Such labels are themselves well known in clinical diagnostic chemistry.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*. Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principle indicating group is an enzyme such as HRP or glucose oxidase, additional reagents are required to indicate that a receptor-ligand complex (immunoreactant) has formed. Such additional reagents for HRP include hydrogen peroxide and an oxidation dye precursor such as diaminobenzidine. An additional reagent useful with glucose oxidase is 2,2,-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. Also useful is a beta emitter, such $^{111}$indium or $^{3}$H. Catalytic antibodies which do or do not bind to the activation site region of apolipoprotein(a) can also be employed for labeling purposes.

The linking of labels, i.e., labeling of peptides and proteins is well known in the art. For instance, monoclonal antibodies produced by a hybridoma can be labeled by metabolic incorporation of radioisotope-containing amino acids provided as a component in the culture medium. See, for example, Galfre et al., Meth. Enzymol., 73:3–46 (1981). The techniques of protein conjugation or coupling through activated functional groups are particularly applicable. See, for example, Aurameas et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a "specific binding agent," which is a molecular entity capable of selectively binding an antibody or peptide of this invention or a complex containing such a species, but is not itself a peptide or antibody of this invention. Exemplary specific binding agents are second antibody molecules, complement proteins or fragments thereof, *S. aureus* protein A, and the like. Preferably the specific binding agent binds the antibody or peptide when it is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a complex.

The diagnostic kits can also include proteases such as urokinase, streptokinase or t-PA.

The diagnostic kits of the present invention can be used in an "ELISA" format to detect the quantity of lipoprotein(a) or apolipoprotein(a) in a vascular fluid sample such as blood, serum, or plasma. "ELISA" refers to an enzyme linked immunosorbent assay such as those discussed above, which employ an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology*, D. P. Sites et al., Lange Medical Publications of Los Altos, Calif. (1982), and in U.S. Pat. Nos. 3,654,090, 3,850,752, and 4,016,043, which are all incorporated herein by reference.

Thus, in preferred embodiments, a peptide or antibody of this invention can be affixed to a solid matrix to form a solid support. A reagent is typically affixed to a solid matrix by adsorption from an aqueous medium although other modes of affixation applicable to proteins and peptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; polystyrene beads about 1 micron to about 5 millimeters in diameter polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The peptide, antibody, proteases, specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package. A solid support such as the above-described microtiter plate and one or more buffers can also be included as separately packaged elements in the diagnostic assay systems of this invention.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

F. Therapeutic Compositions

The peptides, constructs and antibodies of this invention can also be used for therapeutic purposes. For example, the antibodies can be used by themselves, or they can be used to prepare therapeutic conjugates in which an antibody is conjugated to an agent which in some way alters lipoprotein(a), e.g., by cleavage, or which provokes an immune response to the apolipoprotein(a)-conjugate complex such that the entire complex is destroyed or removed by the host's immune system. In this way, the presence of lipoprotein(a) in the bloodstream could be reduced. When preparing such conjugates, it is preferred that the antibodies used exhibit substantially no cross reactivity toward plasminogen, which is an essential component of the blood.

Agents which can be conjugated to antibodies to provoke an immune response include toxins such as diphtheria toxin and vaccinia virus, which are commonly recognized by the body (of immunized persons) and eliminated by the immune system.

The peptides and constructs of this invention can be used to provoke a temporary or prolonged immune response in a host mammal against lipoprotein(a). Those skilled in the art of preparing pharmaceutical compositions will realize how to prepare the antibodies, conjugates, peptides and constructs described above for pharmaceutical use using accepted pharmaceutical carriers.

The following Examples are provided solely for illustrative purposes, and do not in any manner limit this invention.

EXAMPLE 1

SYNTHESIS OF A LIPOPROTEIN(a) PEPTIDE CONSTRUCT CORE

One gram of t-butoxycarbonyl (Boc) βala-OCH$_2$-PAM resin, substituted with β-alanine at a level of 0.01 millimole per gram of resin, was prepared according to the procedure of Merrifield et al. (*J. Org. Chem.* 43: 2845–2852 (1978)). The Boc protective group was removed by treatment of the resin with three changes of 15 ml trifluoroacetic acid in dichloromethane (1:1) for a total of 60 minutes at 22° C. The resin was then neutralized by treatment with 20 ml triethylamine in dichloromethane (1:9) for 20 minutes at 22° C., washed 3 times with 20 ml of dichloromethane and 3 times with 20 ml of dimethylformamide and placed into a solid state synthesis reaction vessel.

A symmetrical anhydride of $N_\alpha,N_\epsilon$-di t-Boc-L-lysine was prepared by dissolving 1 millimole of $N_\alpha,N_\epsilon$-di t-Boc-L-lysine in 3 ml dimethylformamide. The solution was cooled to 0° C. and 2 ml dimethylformamide containing 2 millimoles of dicyclohexylcarbodiimide at 0° C. was added. The reaction was allowed to proceed for one hour at 0° C. and the solution was then warmed to 22° C. The anhydride was then filtered through a Buchner funnel onto the resin sample and the reaction vessel was then rocked at 18 cycles per minute for 2 hours at 22° C. A sample of approximately 1 mg of the resin was then removed and assayed for completeness of reaction using the ninhydrin procedure described by Merrifield et al., (*Analytical Biochemistry*, 117: 147–157 (1981)). A second coupling was performed to force the reaction to a more complete state by equilibrating the resin in dichloromethane, adding 1 millimole of $N_{60},N_\epsilon$-di t-Boc-L-lysine in 5 ml dichloromethane, rocking for 10 minutes at 22° C., adding 2 millimoles of dicyclohexylcarbodiimide and rocking for 17 hours at 22° C. A subsequent ninhydrin assay indicated better than 99% completeness of reaction.

The Boc protective groups were then removed by treating the resin with 15 ml of a 1:1 solution of trifluoroacetic acid in dichloromethane containing 1 mg per ml of indole for 30 minutes with one change of reaction solvent at 15 minutes. The resin was then neutralized by treatment with 15 ml of 5% diisopropylethylamine in dichloromethane for 30 minutes and subsequently washed with three 15 ml aliquots of dichloromethane and three 15 ml aliquots of dimethylformamide.

The addition of the second lysine residue layer to the carrier backbone was accomplished by adding two millimoles of $N_\alpha,N_\epsilon$-di t-Boc-L-lysine to four millimoles of dicyclohexyl-carbodiimide in a total volume of 15 ml of dimethylformamide at 0° C. to form a symmetrical anhydride which was then subsequently reacted with the free amine groups on the resin for 3 hours at 22° C. At the end of the second hour, an additional four millimoles of dicyclohexyl-carbodiimide in dimethylformamide was added. The resin was then washed with dichloromethane (3×20 ml) and the completeness of the reaction was determined by ninhydrin determination of the free amine content. The Boc protective groups were then removed as previously described.

The addition of the third lysine residue layer to the carrier backbone was accomplished by adding four millimoles of $N_\alpha,N_\epsilon$-di t-Boc-L-lysine to eight millimoles of dicyclohexyl-carbodiimide in a total volume of 15 ml of dimethylformamide at 0° C. to form a symmetrical anhydride which was then subsequently reacted with the free amine groups on the resin for one hour at 22° C. The resin was then washed with dichloromethane. Resin aggregates were broken up by passing the resin through a fine stainless steel mesh filter, and the coupling was reinitiated using the identical reaction conditions stated above, but substituting dichloromethane for dimethylformamide. Reaction of the lysine residues with the resin free amines was shown to be better than 99% complete by ninhydrin analysis. The resin was treated with trifluoroacetic acid: dichloromethane with 1 mg per ml of indole to remove the Boc protective groups. A quantitative ninhydrin analysis of the deprotected resin indicated an amine content of 0.08 millimole per gram or eight times the free amine content of the starting material, consistent with the proposed structure of the lysine backbone as shown in FIG. 1.

A triglycine chain extender was now added to each free amine group by the sequential addition of three glycine residues. A solution was prepared by dissolving 0.7 millimole of Boc-glycine in 3 ml of dimethylformamide. The solution was cooled to 4° C. and 0.7 millimole 1-(3-dimethylaminopropyl)-3-ethylcarbodiimide in 7 ml of dimethylformamide was added. The solution was allowed to stand for 1 hour at 4° C., warmed to 22° C. and filtered onto the resin which was then rocked for 2 hours at 22° C. The resin was then checked for completeness of coupling using the ninhydrin assay for free amines. If the reaction was not complete the resin was washed with dichloromethane and the coupling procedure reinitiated as described above. When the reaction was found to be better than 99% complete the Boc groups were removed using the trifluoroacetic acid: dichloromethane: indole procedure as previously described and the next glycine residue added as above until the following structure was prepared:

Resin-PAM-CH$_2$O-βAla-K-K$_2$-K$_4$-(GGG-NH$_2$)$_8$

This structure constitutes the core of the Lp(a) peptide construct.

EXAMPLE 2

SYNTHESIS OF A LIPOPROTEIN(a) PEPTIDE ONTO THE CORE CONSTRUCT

For synthesis of the lipoprotein(a) peptide onto the core construct, α-amino-Boc-protected amino acids were used exclusively. Other protecting groups used were p-methoxybenzyl protection on L-cysteine, O-benzyl on L-serine, ε-carbobenzoxyl on L-lysine and a Γ-benzyl ester on L-glutamic acid.

The general coupling reaction used involved preparing a symmetrical anhydride of the requisite amino acid by dissolving 0.4 millimole of the Boc-protected amino acid in 3–5 ml of dichloromethane and cooling the resultant solution to 4° C. To this was added 2 millimoles of dicyclohexylcarbodiimide dissolved in 10 ml of dichloromethane and the reagents were allowed to react for 1 hour at 4° C. The solution was then warmed to 22° C. and filtered onto the resin which had previously been equilibrated in dichloromethane. The resin was then rocked with the anhydride solution for 1–2 hours at 22° C. A sample of the resin was then removed and the completeness of the reaction determined by ninhydrin analysis. If the reaction was found to be less than 95% complete, a second coupling was performed using the identical procedure substituting dimethylformamide for dichloromethane.

For coupling N-t-Boc-L-glycine, 1-(3-dimethylaminopropyl)-3-ethylcarbodiimide was substituted for dicyclohexylcarbodiimide. For coupling N-t-Boc-L-glutamic acid Γ-benzyl ester, 0.4 millimole of the amino acid was dissolved in 5 ml dichloromethane and then added to the resin which was then rocked for 5 minutes at 22° C. To this was then added 2 millimoles of dicyclohexyl-carbodiimide dissolved in 7 ml dichloromethane and the resin was rocked for 18 hours at 22° C. to provide an acceptable degree of coupling.

Following each successful coupling step the Boc protective group was removed by rocking the resin for 30 minutes in 15 ml of trifluoroacetic acid: dichloromethane (1:1) solution containing 1 mg/ml indole, rinsing the resin with 6 changes of 15 ml dichloromethane, neutralizing the resin for 20 minutes with 2 changes of 15 ml of a 5% solution of diisopropylethylamine in dichloromethane and rinsing the resin with 3 changes of 20 ml dichloromethane.

The structure of the core construct with the synthesized peptide was as follows:

RESIN-PAM-CH$_2$O-βAla-KK$_2$K$_4$-(GGGAVCGGVISG-PCKKPE-NH$_2$)$_8$.

A quantitative ninhydrin assay performed in duplicate on the completed structure indicated free amine contents of 0.087 and 0.103 millimole per gram versus an anticipated 0.08 millimole per gram by prior analysis on the unreacted resin.

The peptide construct was then acylated to neutralize the charge on the N-terminal amino group. A solution was prepared consisting of 3 mM acetic anhydride in dimethylformamide with 3 millimoles of 4-dimethylaminopyridine. The resin containing the peptide construct was rocked with 15 ml of this reagent for 30 minutes at 22° C. The resin was then washed with dimethylformamide. A resin sample assayed using the ninhydrin procedure indicated the absence of free amino residues on the peptide construct.

EXAMPLE 3

CLEAVAGE OF THE CONSTRUCT FROM THE RESIN AND PREPARATION FOR IMMUNIZATION

The resin containing the peptide construct was treated with 20 ml of a trifluoromethanesulfonic acid: trifluoroacetic acid: dimethylsulfide: m-cresol solution (1:5:3:1 v/v) for 4 hours at 0° C. Thirty milliliters of a 1% solution of β-mercaptoethanol in anhydrous ether cooled to −5° C. was then added and thoroughly mixed with the reaction mixture. The mixture was then transferred to a 250 ml separation flask and the construct was extracted by shaking the reaction solution with 100 ml of 0.1M tris buffer, pH 8.0 containing 8M urea and 0.2M dithiothreitol. The layers were allowed to separate and the aqueous layer was placed in Spectra por dialysis tubing (1000 M$_r$ cutoff) and dialyzed successively overnight against 0.1M ammonium carbonate buffer, pH 8.0 with 0.1M β-mercaptoethanol and 8M urea; 0.1M ammonium carbonate buffer, pH 8.0 with 8M urea; 0.1M ammonium carbonate buffer, Ph 8.0 with 2M urea; water; and 1M acetic acid.

The material (in 1M acetic acid) was then lyophilized, the recovered material analyzed for amino acid content and used without further purification. The result of the amino acid analysis was as follows:

| Amino Acid | Ratio Expected | Ratio Found |
|---|---|---|
| E | 8 | 8.34 |
| S | 8 | 8.64 |
| G | 48 | 58.90 |
| A + βA | 9 | 11.30 |
| P | 16 | 16.90 |
| V | 16 | 16.20 |
| C | 16 | PRESENT |
| I | 8 | 5.80 |
| K | 23 | 25.90 |

EXAMPLE 4

IMMUNIZATION OF MICE WITH THE PEPTIDE CONSTRUCT

Adult BALB/C mice were injected with the peptide construct as prepared in Example 3. Each mouse received 50 micrograms of the lyophilized peptide dissolved in 1 ml of complete Freund's adjuvant (administered 0.5 ml intraperitoneally and 0.5 ml subcutaneously). Serum was collected from one eye of each mouse 30 days after peptide injection and tested for antibodies to the peptide construct by a microplate EIA (enzyme immunoassay) as described in Example 6 and for antibodies to lipoprotein(a) by an Ouchterlony immunoprecipitation assay as described in Example 9. Mice which tested positive for antibodies against the peptide construct by microplate EIA were reinoculated 4 days prior to cell fusion by injection of 50 micrograms of the peptide construct into the tail vein (in PBS, 0.2 ml per mouse).

EXAMPLE 5

PRODUCTION OF HYBRIDOMAS BY FUSION OF IMMUNE MOUSE SPLEEN CELLS WITH MOUSE MYELOMA CELLS

Mouse myeloma cells (SP2/0-Ag-14) were grown from frozen seed stock previously passaged in Opti-MEM® (Gibco #320-1985) containing 8-azaguanine. The cells were thawed and grown in Optimem media (Opti-MEM® with 0.1% β-mercaptoethanol, 1 mM L-glutamine, 1 mcg/ml Fungizone, 0.05 mg/ml gentamicin sulfate and 6% FBS (fetal bovine serum)) for 2 days prior to fusion. The cells were then collected by centrifugation and washed in cold (4° C.) Optimem media without FBS. A cell sample was removed and viability was checked by trypan blue exclusion (95+% viability). The cells were then centrifuged and resuspended in cold Optimem media without FBS two more times and finally resuspended in cold Optimem media without FBS.

The mice from Example 4 which tested positive for antibodies to the peptide construct were sacrificed by cervical dislocation. The spleens were removed under aseptic conditions, washed with cold Optimem media without FBS, placed into a mesh grinding cup over a conical tube on ice and minced with scissors. The cells were forced through the mesh with a glass rod and rinsed into the tube with ACK buffer (7 mM carbonate buffer, pH 7.4 with 0.15M ammonium chloride and 0.01M EDTA (ethylenediamine tetraacetic acid)). The cells were allowed to stand for 10 minutes, pelleted by centrifugation and resuspended in 50 ml of cold Optimem without FBS. Clotted material was removed with a 10 ml pipette. An aliquot of cells was removed, diluted 1:10 with Optimem and the number of viable spleen cells determined by trypan blue exclusion. The spleen cells were then mixed in a round-bottomed tube with SP2/0 cells to achieve a ratio of 3:1.

The cells were pelleted by centrifugation and the supernatant was poured off. The tube was then placed into a 37° C. water bath and gently tapped until the cell pellet formed a smooth slurry. To this was then added 2 ml of 37° C. polyethylene glycol (mw 1,500) slowly over a 1 minute period with gentle agitation to mix the solution with the slurry. The cells were then pelleted by centrifugation and 2 ml of 37° C. Optimem media without FBS was slowly added over 1 minute followed by the addition of 10 ml more of the same solution over the next two minutes. The cells and solution were transferred to a 50 ml conical tube and an additional 10 ml of 37° C. serumless Optimem media was added slowly. The cells were then pelleted and resuspended in 25 ml of 2×HAT medium (4% solution of 50×HAT (B. Mannheim) in Optimem media containing 15% MRC-5 conditioned EMEM/NEAA medium). The cells were then diluted into 100–150 ml of 2×HAT medium and dispensed into 96 well polystyrene microplates at 0.1 ml per well. The microplates were then placed into a water-jacketed $CO_2$ incubator at 37° C. and 5% $CO_2$. On days 4, 7 and 10 post fusion the medium was changed with 1×HAT (2% solution of 50×HAT in Optimem media containing 15% MRC-5 conditioned EMEM/NEAA medium) using 0.1 ml per well.

When visible colonies appeared, all of the wells were tested for production of antibodies to the peptide construct by the enzyme immunoassay described below in Example 6. Those cells showing elevated activity in the enzyme immunoassay were subcloned twice and grown out to eliminate non-producing cells. After 2 subclones the cells were tested for production of antibodies to the lipoprotein(a) (Example 7) by the enzyme immunoassay described below in Example 8.

EXAMPLE 6

ENZYME IMMUNOASSAY TO DETECT ANTIBODIES TO THE APOLIPOPROTEIN(a) PEPTIDE CONSTRUCT

For this assay, peptide construct dissolved in 0.1M sodium carbonate buffer, pH 9.0 was incubated for 18 hours at 37° C. in a polystyrene 96 well microplate (0.5 microgram peptide construct per 0.12 ml per well). The plate was then washed 3 times with wash buffer (5% lactose solution containing 0.5% BSA (bovine serum albumin) and 0.1% sodium azide). The plates were then stored at 4° C. with 0.2 ml of wash buffer in each well until required for an assay. Prior to an assay the wash buffer was removed and the plates dried by inverting them and tapping them on a paper towel until no droplets were observed inside the wells.

Sera to be assayed (from mice immunized with peptide construct in Example 4) was diluted 1:50 with sample dilution buffer (phosphate buffered saline (PBS), pH 7.0 containing 1% BSA, 0.1% sodium azide and 0.1 Triton X-705) and 0.12 ml aliquots of the diluted samples were added to wells in the assay plate. The plate was covered and warmed to 37° C. for 1 hour. The plate was then washed with assay wash buffer (0.3M TRIS buffer, pH 8.0 with 1.2M ammonium sulfate, 0.12M magnesium chloride, 0.001M zinc chloride, 0.1% sodium azide and 0.001% Triton X-705), drained and tapped dry.

To each well was then added 0.1 ml of alkaline phosphatase-labeled goat anti-mouse IgG diluted 1:500 with PBS. The plate was then incubated for 1 hour at 37° C., washed four times with assay wash buffer, drained and tapped dry. The presence of alkaline phosphatase activity was determined by the addition of 0.1 ml of substrate solution (p-nitrophenylphosphate in diethanolamine buffer; Kirkegaard & Perry Laboratories, Inc., Gaithersburg, Md.) to each well followed by incubation at room temperature for 30 minutes. When the most reactive well achieved an absorbance of 1.5–2.0 at 410 nm the reaction in all wells was stopped by the addition of 0.1 ml 5% EDTA. The absorbance at 410 nm of each well was determined and recorded using a Dynatech MR-300 ELISA plate reader. A sample was deemed positive if the $OD_{410}$ was greater than 0.05 absorbance units when compared to the absorbance of a well containing no peptide construct coating.

EXAMPLE 7

ISOLATION AND PURIFICATION OF LIPOPROTEIN(a) FROM HUMAN SERUM

A plasma sample was obtained from a single donor who had tested positive for the presence of lipoprotein(a) by the enzyme immunoassay described in Example 10. Sixty-five ml of the sample was centrifuged at 105,000×g for 24 hours at 10° C. The floating layer was removed and the infranatant solution was brought back to a total volume of 65 ml with deionized water. To this solution was then added 0.715 ml of a 100 mg per ml solution of high molecular weight dextran sulfate (mw 500,000) and 7.15 ml of 1M calcium chloride. The solution was allowed to precipitate for 1 hour at 4° C. The solids were removed by centrifugation at 1,600×g for 15 minutes at 10° C. The upper solution was poured off and the solids were allowed to dissolve overnight in 60 ml of a sodium chloride solution (1.12 kg/L density at 10° C.) containing 0.1 mM EDTA and 0.1 mM PMSF (phenylmethylsulfonylfluoride). The solution was then centrifuged at 105,000×g for 23 hours at 10° C. The upper layer was removed, placed in Spectra por 7 dialysis tubing ($M_r$-8,000 cutoff) and dialyzed against a sodium chloride solution (1.05 kg/L density at 10° C.) containing 0.1 mM EDTA and 0.1 mM PMSF for 48 hours and 2 changes of dialysis fluid at 10° C. The dialysate was then centrifuged at 105,000×g for 72 hours at 10° C. The floating material was removed and the infranatant solution, containing the lipoprotein(a), was stored at 4° for further use.

EXAMPLE 8

ENZYME IMMUNOASSAY TO DETECT ANTIBODIES TO NATIVE LIPOPROTEIN(a)

For this assay, isolated Lp(a) from Example 7 was diluted 1:256 with 0.1M sodium carbonate buffer, pH 9.0. This solution was then placed into a 96 well polystyrene microplate (0.3 microgram protein per 0.12 ml per well) and incubated for 18 hours at 37° C. The plate was then washed 4 times with wash buffer (5% lactose solution with 0.5% BSA and 0.1% sodium azide). The plates were then stored at 4° C. with 0.2 ml of wash buffer in each well until required for an assay. Prior to an assay the wash buffer was removed and the plates dried by inverting them and tapping them on a paper towel until no droplets were observed inside the wells.

Sera to be assayed were diluted 1:50 with sample dilution buffer (PBS, pH 7.0 containing 1% BSA, 0.1% sodium azide and 0.1% Triton X-705) and 0.12 ml aliquots of the diluted samples were added to the wells in the assay plate. The plate was covered and warmed to 37° C. for 2 hours. The plate was then washed with assay wash buffer (0.3M TRIS buffer, pH 8.0 with 1.2M ammonium sulfate, 0.12M magnesium chloride, 0.001M zinc chloride, 0.1% sodium azide and 0.001% Triton X-705), drained and tapped dry.

To each well was then added 0.1 ml of alkaline phosphatase-labeled goat anti-mouse IgG diluted 1:500 with PBS. The plate was then incubated for 1 hour at 37° C., washed four times with assay wash buffer, drained and tapped dry. The presence of alkaline phosphatase activity was determined by the addition of 0.1 ml of substrate solution (p-nitrophenylphosphate in diethanolamine buffer; Kirkegaard & Perry Laboratories, Inc., Gaithersburg, Md.) to each well followed by incubation at room temperature for 30 minutes. When the most reactive well achieved an absorbance of 1.5–2.0 at 410 nm the reaction in all wells was stopped by the addition of 0.1 ml 5% EDTA. The absorbance at 410 nm of each well was determined and recorded using a Dynatech MR-300 ELISA plate reader. A sample was deemed positive if the $OD_{410}$ was greater than 0.05 absorbance units when compared to the absorbance of a well containing no native lipoprotein(a) coating.

EXAMPLE 9

OUCHTERLONY IMMUNODIFFUSION ASSAY

A solution of 1% agarose with 1 mM magnesium and 1 mM calcium is heated to boiling and 2–3 ml is placed onto a microscope slide and allowed to solidify. Upon solidification, holes (3 mm diameter) are punched into the agarose gel using the tip of a Pasteur pipette in a rosette pattern consisting of a central well with eight wells surrounding it at a distance of 5 mm. Purified lipoprotein(a) as prepared in Example 7 in a total volume of 10–15 microliters was placed into the central well. The surrounding wells were filled with 10–15 microliters of sera or culture fluid to be tested for antibodies to lipoprotein(a). The slide was then incubated for 16–24 hours at 37° C. in a 100% humidity chamber. At the end of the incubation time the slide was inspected for the presence of white precipitation lines or areas indicative of antibody:antigen interactions.

EXAMPLE 10

ENZYME IMMUNOASSAY TO DETECT LIPOPROTEIN(a)

For this assay, antibody directed against the peptide construct (Example 5) was diluted in 20 mM Citrate buffer, pH 6.0 and incubated for 18 hours at 37° C. in a polystyrene 96 well microplate (0.6 microgram antibody per 0.12 ml per well). The plate was then washed 3 times with wash buffer (5% lactose solution containing 0.5% BSA (bovine serum albumin) and 0.1% sodium azide). The plates were then stored at 4° C. with 0.2 ml of wash buffer in each well until required for an assay. Prior to an assay the wash buffer was removed and the plates dried by inverting them and tapping them on a paper towel until no droplets were observed inside the wells.

Sera to be assayed were diluted 1:50 with sample dilution buffer (phosphate buffered saline (PBS), pH 7.0 containing 1% BSA, 0.1% sodium azide and 0.1% Triton X-705) and 0.12 ml aliquots of the diluted samples were added to wells in the assay plate. The plate was covered and warmed to 37° C. for 1 hour. The plate was then washed with assay wash buffer (0.3M TRIS buffer, pH 8.0 with 1.2M ammonium sulfate, 0.12M magnesium chloride, 0.001M zinc chloride, 0.1% sodium azide and 0.001% Triton X-705), drained and tapped dry.

To each well was then added 0.1 ml of alkaline phosphatase-labeled sheep anti-human apolipoprotein B-100 IgG diluted 1:1000 with sample dilution buffer. The plate was then incubated for 1 hour at 37° C., washed four times with assay wash buffer, drained and tapped dry. The presence of alkaline phosphatase activity was determined by the addition of 0.1 ml of substrate solution (p-nitrophenylphosphate in diethanolamine buffer; Kirkegaard & Perry Laboratories, Inc., Gaithersburg, Md.) to each well followed by incubation at room temperature for 30 minutes. When the most reactive well achieved an absorbance of 1.5–2.0 at 410 nm the reaction in all wells was stopped by the addition of 0.1 ml 5% EDTA. The absorbance at 410 nm of each well was determined and recorded using a Dynatech MR-300 ELISA plate reader. A sample was deemed positive if the $OD_{410}$ was greater than 0.05 absorbance units when compared to the absorbance of a well containing no antibody coating.

EXAMPLE 11

PREPARATION OF A SYNTHETIC STANDARD

To circumvent the difficulties associated with the preparation of a standard solution of purified, stabilized native lipoprotein(a), the synthesis of a synthetic secondary standard for use in enzyme immunoassays of lipoprotein(a) and apolipoprotein(a) is proposed. An exemplary structure for a synthetic standard for lipoprotein-(a) would be as follows:

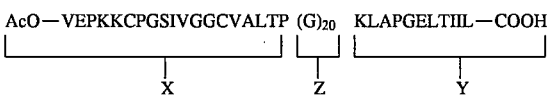

where

X(SEQ ID NO:2)=protease cleavage region of apolipoprotein(a)

Y(SEQ ID NO:3)=C-terminal end of apolipoprotein B-100

Z(SEQ ID NO:14)=spacer region to separate epitopes

An exemplary structure for an apolipoprotein(a) secondary standard would be as follows:

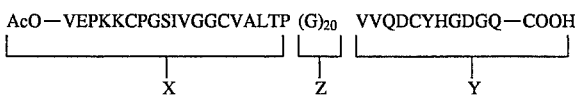

where

X(SEQ ID NO:2)=protease cleavage region of apolipoprotein(a)

Y(SEQ ID NO:4)=C-terminal end of apolipoprotein(a)

Z(SEQ ID NO:14)=spacer region to separate epitopes

While these exemplary secondary standards are designed to interact, respectively, with antibodies directed against the C-terminal regions of apolipoprotein B-100 and apolipoprotein(a) as the second (reporter) antibody in the assay format, other regions of the proteins can be synthesized to provide unique epitopes which can also be used. The glycine spacer region can be altered both in length and in amino acid composition to provide an optimized peptide which will be water soluble and be of sufficient length to negate any steric hindrance between the antibody bound to the solid surface (the capture antibody) and the labelled antibody used to provide the signal which can be related to the quantity of native material bound to the solid support (the reporter antibody).

One advantage of these secondary standards is that the aspects of the immunological interactions which allow the assay to function can be supplied synthetically to provide a model which can reproduce the signal generated by a known amount of target antigen interacting within the system. By determining the signal produced by a (weighed) secondary standard, a relationship can be made to the signal produced by the natural material in the assay, thereby allowing a quantitative determination of the native material.

It will be apparent to those skilled in the art that various modifications and variations can be made to the compositions of matter and methods of this invention. Thus, it is intended that the present invention cover the modifications and variations of this invention provided they come within the scope of the appended claims and their equivalents.

What is claimed is:

1. A method for provoking an immune response against apolipoprotein(a), comprising administering to a mammal an immune response provoking amount of a peptide bound to a carrier, said peptide bound carrier comprising the following structure:

βAla-Lys-(Lys$_2$)-(Lys$_4$)-((Gly$_3$)-Ala-Val-Cys-Gly-Gly-Val-Ile-Ser-Gly-Pro-Cys-Lys-Lys-Pro-Glu-OAc)$_8$.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:1:

```
Glu  Pro  Lys  Lys  Cys  Pro  Gly  Ser  Ile  Val  Gly  Gly  Cys  Val  Ala
1                   5                        10                       15
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Val  Glu  Pro  Lys  Lys  Cys  Pro  Gly  Ser  Ile  Val  Gly  Gly  Cys  Val  Ala
1                   5                        10                       15

Leu  Thr  Pro
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Lys  Leu  Ala  Pro  Gly  Glu  Leu  Thr  Ile  Ile  Leu
1                   5                        10
```

( 2 ) INFORMATION FOR SEQ ID NO:4:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:4:

```
Val Val Gln Asp Cys Tyr His Gly Asp Gly Gln
 1               5                   10
```

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:5:

```
Lys Cys Pro Gly Arg Val Val Gly Gly
 1               5
```

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:6:

```
Lys Cys Pro Gly Ser Ile Val Gly Gly
 1               5
```

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:7:

```
Lys Cys Pro Gly
 1
```

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:8:

```
Lys Lys Cys Pro Gly
 1               5
```

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (x i) SEQUENCE DESCRIPTION: SEQ ID NO:9:

Pro Lys Lys Cys Pro Gly
1               5

(2) INFORMATION FOR SEQ ID NO:10:

(i) SEQUENCE CHARACTERISTICS:
   (A) LENGTH: 7 amino acids
   (B) TYPE: amino acid
   (D) TOPOLOGY: linear (i i) MOLECULE TYPE: peptide (x i) SEQUENCE DESCRIPTION: SEQ ID NO:10:

Glu Pro Lys Lys Cys Pro Gly
1               5

(2) INFORMATION FOR SEQ ID NO:11:

(i) SEQUENCE CHARACTERISTICS:
   (A) LENGTH: 4 amino acids
   (B) TYPE: amino acid
   (D) TOPOLOGY: linear (i i) MOLECULE TYPE: peptide (x i) SEQUENCE DESCRIPTION: SEQ ID NO:11:

Val Gly Gly Cys
1

(2) INFORMATION FOR SEQ ID NO:12:

(i) SEQUENCE CHARACTERISTICS:
   (A) LENGTH: 5 amino acids
   (B) TYPE: amino acid
   (D) TOPOLOGY: linear (i i) MOLECULE TYPE: peptide (x i) SEQUENCE DESCRIPTION: SEQ ID NO:12:

Val Gly Gly Cys Val
1               5

(2) INFORMATION FOR SEQ ID NO:13:

(i) SEQUENCE CHARACTERISTICS:
   (A) LENGTH: 6 amino acids
   (B) TYPE: amino acid
   (D) TOPOLOGY: linear (i i) MOLECULE TYPE: peptide (x i) SEQUENCE DESCRIPTION: SEQ ID NO:13:

Val Gly Gly Cys Val Ala
1               5

(2) INFORMATION FOR SEQ ID NO:14:

(i) SEQUENCE CHARACTERISTICS:
   (A) LENGTH: 20 amino acids
   (B) TYPE: amino acid
   (D) TOPOLOGY: linear (i i) MOLECULE TYPE: peptide (x i) SEQUENCE DESCRIPTION: SEQ ID NO:14:

-continued

| Gly | Gly | Gly | Gly | Gly | Gly | Gly | Gly | Gly | Gly | Gly | Gly | Gly | Gly | Gly | Gly |
| 1 | | | | 5 | | | | | 10 | | | | | 15 | |
| Gly | Gly | Gly | Gly | | | | | | | | | | | | |
| | | | 20 | | | | | | | | | | | | |